United States Patent [19]
Rueggeberg et al.

[11] Patent Number: 5,800,163
[45] Date of Patent: Sep. 1, 1998

[54] METHOD AND APPARATUS FOR LIGHT-CURING RESIN ADHESIVES FOR ORTHODONTIC BRACKETS

[75] Inventors: Frederick A. Rueggeberg, Augusta; Thomas C. Whaley, Mableton, both of Ga.

[73] Assignee: MCG Research Institute, Augusta, Ga.

[21] Appl. No.: 816,619

[22] Filed: Mar. 13, 1997

[51] Int. Cl.⁶ .................................................. A61C 3/00
[52] U.S. Cl. .................................................. 433/9; 433/29
[58] Field of Search ................................ 433/8, 9, 141, 433/229, 29

[56] References Cited

U.S. PATENT DOCUMENTS

| | | | |
|---|---|---|---|
| 4,063,360 | 12/1977 | Waller | 433/9 |
| 4,522,594 | 6/1985 | Stark et al. | 433/141 |
| 4,666,406 | 5/1987 | Kanca, III | 433/229 |
| 4,673,353 | 6/1987 | Nevin | 433/90 |
| 4,749,352 | 6/1988 | Nicholson | 433/9 |
| 4,836,782 | 6/1989 | Gonser | 433/229 |
| 4,888,489 | 12/1989 | Bryan | 250/504 H |
| 4,948,215 | 8/1990 | Friedman | 350/96.1 |
| 5,030,093 | 7/1991 | Mitnick | 433/164 |
| 5,049,068 | 9/1991 | Sterrett et al. | 433/9 |
| 5,198,678 | 3/1993 | Oppawsky | 250/455.11 |
| 5,290,169 | 3/1994 | Friedman et al. | 433/29 |
| 5,388,988 | 2/1995 | Goisser et al. | 433/29 |

*Primary Examiner*—Nicholas D. Lucchesi
*Attorney, Agent, or Firm*—Needle & Rosenberg, P.C.

[57] ABSTRACT

A method and apparatus for curing an adhesive resin by use of light in which the resin is disposed between a bottom surface of an orthodontic bracket and a tooth surface, wherein a curing tip enhancer of the present invention directs the light onto the adhesive when the bracket is disposed within a portion of the curing tip enhancer. Preferably, the light is directed onto the adhesive resin in a direction substantially parallel to the tooth surface. A portion of the interior surface of the bore of the curing tip enhancer is disposed at an angle so that the light is reflected onto the resin. A light-reflective interior surface of the bore increases the effectiveness of the curing tip enhancer because more radiant energy is reflected onto the resin.

17 Claims, 2 Drawing Sheets

METHOD AND APPARATUS FOR LIGHT-CURING RESIN ADHESIVES FOR ORTHODONTIC BRACKETS

BACKGROUND OF THE INVENTION

1. Field of the Invention

The present invention relates to light-curing an adhesive resin that secures an orthodontic bracket to a tooth and, more particularly, to directing light onto the bracket, which is disposed within a portion of the apparatus of the present invention, so that the curing time is reduced by more effectively directing the radiant energy.

2. Background Art

Use of visible light to polymerize a photo-curable adhesive resin is increasing as a method for attaching an orthodontic bracket to a tooth surface. Orthodontists chose to use this technique because of its simplicity and reduction in the time required to attach brackets to a patient's teeth. The adhesive resin used in this method firmly bonds each bracket to its respective tooth.

The prior art method of light-curing resin involves exposing each orthodontic bracket four times in ten-second exposures so that the thin layer of resin disposed on each of the four sides of the bracket base is light-cured.

Light often cannot penetrate through the bracket, which is frequently constructed of metal or opaque plastic. Thus, repeating the ten-second exposure sequence four times for each bracket is necessary to obtain sufficient bonding strength. That is, since the light cannot penetrate through the bracket, the radiant energy source must be positioned around the bracket to be directed at the resin or, otherwise, the bracket would block the light. Although it is possible to use a translucent or transparent orthodontic bracket material, the majority of orthodontic brackets are constructed of stainless steel, which blocks visible light.

Some devices focus the light prior to directing it onto the brackets. These devices, which fall into the general category of "sun guns," produce a collimated light beam. Examples of these prior art devices are shown in U.S. Pat. Nos. 5,049,068, issued to Sterrett et al.; 4,836,782, issued to Gosner; and 4,948,215, issued to Friedman. The collimated light should be directed so that it is parallel to the bracket base to be most effective. Illumination of all sides of a bracket, accordingly, requires maneuvering the device to aim the beam at successive portions of the bracket. Unfortunately, positioning the prior art devices to direct the light is sometimes awkward, if not impossible, because of anatomical restrictions in the patient's mouth combined with restrictions on the size of the curing light. Moreover, this method is time-consuming and not fully reproducible from tooth to tooth and patient to patient. These drawbacks decrease the effectiveness of the light-curing and increase the installation time.

Therefore, a need exists in the art to increase the effectiveness of the light in reaching the bracket base. Also, there is an associated need in the art to decrease the time necessary to install orthodontic brackets in a patient's mouth.

It is also desired that an apparatus for light-curing orthodontic brackets be inexpensive, preferably an attachment installed over a conventional light-curing tip currently used in an orthodontist's office. An associated consideration is that the acquisition cost of such a device is minimal. Moreover, it is desired that the apparatus be reusable to reduce the operating cost further.

SUMMARY OF THE INVENTION

The above disadvantages of the prior art are overcome by the present invention which provides a method and apparatus for curing an adhesive resin with light. The apparatus comprises a curing tip enhancer and a means for directing the light onto the adhesive when the bracket is disposed within a portion of the curing tip enhancer.

The curing tip enhancer has a longitudinally extending bore therethrough. At one end of the bore, a light source is attached so that at least a portion of the light enters into the bore. The opposite end of the bore is of a size to receive the orthodontic bracket therein. The directing means directs, or focuses, the light onto the adhesive resin when the orthodontic bracket is disposed within the bore. Preferably, the directing means directs the light onto the adhesive so that the light is substantially parallel to the tooth surface.

The directing means preferably comprises a portion of the interior surface of the bore adjacent the distal end of the curing tip enhancer being light-reflective and being disposed at an angle, or beveled, relative to the tooth surface. Alternatively, the directing means may comprise a portion of the interior surface of the bore adjacent the distal end of the curing tip enhancer being curved inwardly. It is preferred that the interior surface of the bore be a polished metal surface or have a reflective coating disposed over it. The light-reflective interior surface of the bore increases the effectiveness of the curing tip enhancer because more radiant energy is reflected onto the resin.

The present invention solves many of the problems currently associated with the use of visible light-curing of opaque orthodontic brackets. The tip attachment of the present invention is designed to be used directly over the conventional light-curing tip currently present in an orthodontist's office.

The present invention maximizes the light energy directed at the bonding adhesive area, and, accordingly, decreases the time required to achieve bond strengths which are similar to those obtained through the prior art methods. The enhancer tip of the present invention simultaneously exposes the total periphery of the bracket base to light. Thus, instead of requiring four ten-second exposures, the same bonding strength may be achieved using the present invention for a single twenty-second exposure.

The present invention, therefore, reduces the time to bond brackets to teeth by at least one-half. The prior art methods require forty seconds per tooth, resulting in a time of 26.7 minutes for bonding with light directed onto the brackets for forty teeth. The present invention, in comparison, reduces this time to 13.3 minutes. Thus, an orthodontist or his assistant could see twice the number of patients using the present invention compared to the prior art devices.

As one skilled in the art will also appreciate, there is an additional reduction in the time to light cure the resin because the present invention only requires positioning once, whereas the prior art devices require moving the light source four times to cure each bracket.

DETAILED DESCRIPTION OF THE INVENTION

The present invention is more particularly described in the following examples which are intended as illustrative only since numerous modifications and variations therein will be apparent to one skilled in the art. As used in the specification and in the claims, "a" can mean one or more, depending upon the context that it is used.

Figure 1:
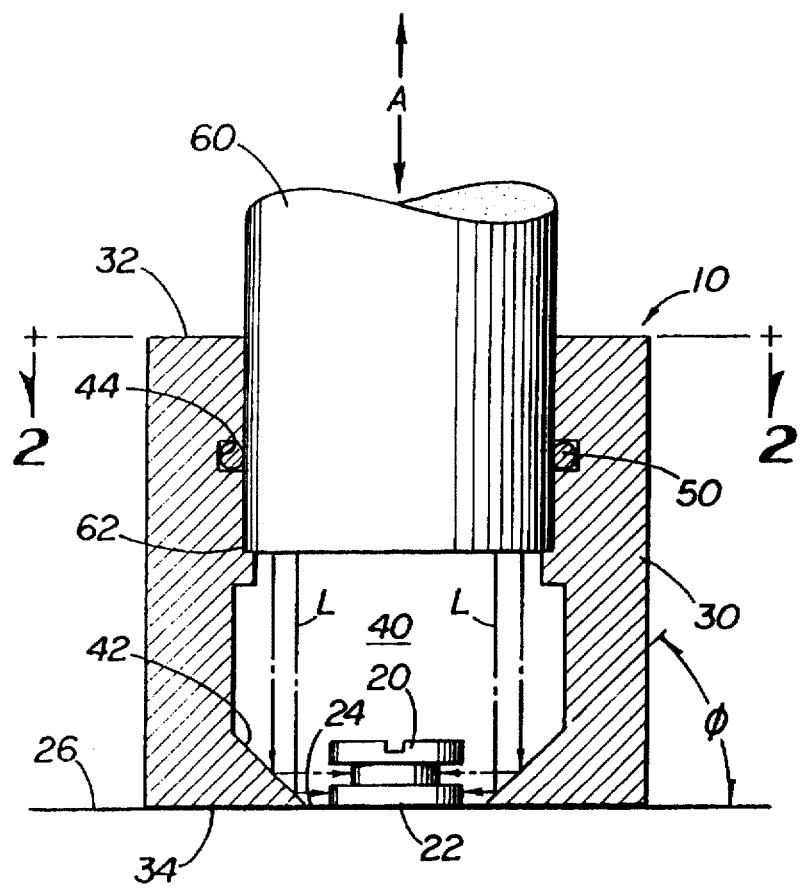
FIG. 1 is a side cross-sectional view showing an apparatus of the present invention disposed over a bracket.
Figure 2:
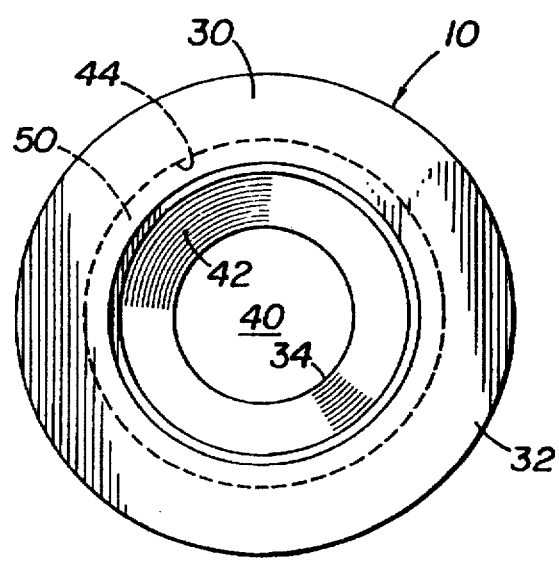
FIG. 2 is a top plan view taken along line 2—2 in FIG. 1, in which the present invention is no longer disposed over the bracket.

Referring first to FIGS. 1 and 2, the present invention comprises an apparatus and method for curing an adhesive resin 24 by use of light (shown in phantom lines as L) in which the resin 24 is disposed at the interface between a bottom surface 22 of an orthodontic bracket 20 and a tooth surface 26. The apparatus comprises a curing tip enhancer 10, which is also called a light enhancer, and a means 42 for directing the light onto the adhesive when the bracket 20 is disposed within a portion of the curing tip enhancer 10.

The curing tip enhancer 10 has a body portion 30 having a proximal end 32 and an opposite, distal end 34. The body portion 30 also defines a longitudinally-extending bore 40 therethrough, which forms an interior surface 42 to the body portion 30. The bore 40 is of a size adjacent its distal end 34 to receive the orthodontic bracket 20 therein so that the bracket 20 is encompassed by and received within a portion of the bore 40.

The directing means 42, which is disposed within the bore 40 of the curing tip enhancer 10, directs, or focuses, the light onto the adhesive resin 24 when the orthodontic bracket 20 is disposed within the bore 40. Preferably, the directing means 42 directs the light onto the adhesive in a direction substantially parallel to the bottom surface 22 of the bracket 20 and the tooth surface 26, as shown in FIG. 1.

Light emits from a first end 62 of a light source 60. The curing tip enhancer 10 of the present invention preferably comprises a means for attaching the first end 62 of the light source 60 to the proximal end 32 of the curing tip enhancer 10 so that at least a portion of the light from the light source 60 enters into the bore 40 of the curing tip enhancer 10. As shown in FIG. 1, all light exiting the first end 62 of the light source 60 is directed into the bore 40 because the first end 62 is disposed within and surrounded by a portion of the bore 40.

Still referring to FIG. 1, the interior surface 42 of the curing tip enhancer 10 adjacent its proximal end 32 has a circumscribing groove 44 therein. The attaching means further comprises an "O" ring 50 disposed in the groove 44 that frictionally engages the first end 62 of the light source 60 with the curing tip enhancer 10. Preferably, the "O" ring 50 is a VITON "O" ring.

The directing means 42 preferably comprises a portion of the interior surface of the bore 40 adjacent the distal end 34 of the curing tip enhancer 10 being light reflective and being disposed at an acute angle, or beveled, relative to the tooth surface 26, which is represented by $\phi$ in FIG. 1. In the preferred embodiment, the angle $\phi$ between the interior surface 42 of the bore 40 adjacent the distal end 34 of the curing tip enhancer 10 and the tooth surface 26 is approximately forty-five degrees (45°).

Alternatively, the directing means may comprise a portion of the interior surface 42 of the bore 40 adjacent the distal end 34 of the curing tip enhancer 10 being light reflective and being curved inwardly (not shown) toward its longitudinal axis A. More specifically, the curved surface of the bore 40 adjacent the distal end 34 is preferably parabolic in cross section taken along the longitudinal axis A, instead of the beveled embodiment shown in FIG. 1.

To best reflect the light from the light source 60, the interior surface 42 of the bore 40 adjacent the distal end 34 of the curing tip enhancer 10 is a polished metal surface or has a reflective coating disposed over it. The light-reflective interior surface 42 of the bore 40, particularly adjacent the distal end 34, increases the effectiveness of the curing tip enhancer 10 because more radiant energy is reflected onto the resin 24.

As shown in FIG. 2, the bore 40 of the curing tip enhancer 10 is circular in cross section. The diameter of the bore 40 of the curing tip enhancer 10 may be of any size, corresponding to the size of the light source 60. In the preferred embodiment the diameter of the bore 40 is between 0.5 and 1 millimeter greater than the diameter of light source 60.

In operation, the method of light-curing adhesive orthodontic brackets 20 using the present invention comprises the steps of first preparing the tooth surface 26 for disposing an orthodontic bracket 20 on it and placing a desired amount of a visible light-curable bonding adhesive between the bottom surface 22 of the bracket 20 and the tooth surface 26. The orthodontist then presses the bracket 20 onto the prepared tooth surface 26.

The next steps entail the orthodontist positioning the curing tip enhancer 10 over the bracket 20 and then actuating the light source 60 to cure the adhesive resin 24 disposed within the bore 40 of the curing tip enhancer 10 for a predetermined time at a selected light intensity. Based on experimentation with a prototype of the present invention, the preferred predetermined time was twenty (20) seconds at a selected light intensity of 350 mW/cm$^2$. One skilled in the art will appreciate that the exposure time will vary as a function of, inter alia, the light intensity, the resin adhesive used and its curing characteristics, the amount of light reflected within the bore 40 toward the bracket 20, the direction that the light is reflected onto the resin, the profile of the bracket 20 itself, and the translucence of the material of which the bracket 20 is formed.

EXAMPLES

The inventors used a prototype of the present invention to perform shear bond strength tests on bovine teeth. The prototype was made by milling stock aluminum rod to specific dimensions in order to accept a commercial light-curing unit tip, specifically an 8 mm 60° fiber optic probe, item #644712, Caulk/Dentsply, Milford, Del. The prototype was compared to a straight cone that lacked an internal bevel to direct the light and other methods known in the prior art.

Before performing the tests, mandibular anterior bovine teeth were extracted and the facial enamel surface was ground flat to a 600 grit silicon carbide finish. The facial enamel was then acid etched (Ultra-Etch, 35% phosphoric acid gel, Ultradent Products, Inc.) for thirty (30) seconds, rinsed, and air-dried to demonstrate a frosted appearance. Unfilled bonding resin (Adhesive Primer, Transbond Light Cured Orthodontic Adhesive, Unitek/3M, Monrovia, Calif.) was applied to the freshly etched and dried tooth surface and was then spread into a thin layer using an application brush. This bonding resin was then photo-cured (Max Lite, Model 100, Caulk/Dentsply, Milford, Del.) for twenty (20) seconds. The light intensity exiting the six (6) millimeter diameter curing tip was approximately 350 mW/cm$^2$ (Model 100, Curing Radiometer, Demetron Research Corp., Danbury, Conn.). A small amount of visible light-cured orthodontic bracket bonding adhesive (Adhesive Paste, Transbond Light Cured Orthodontic Adhesive, lot #317CA, Unitek/3M, Monrovia, Calif.) was placed on the mesh of a stainless steel bracket (A5701 to D2500, Upper left central incisor stainless steel bracket, Rocky Mountain Orthodontics, Inc., Denver, Colo.). The bracket was pressed onto the tooth surface using finger pressure, and the excess paste was removed using a scalpel blade.

The bracket adhesive was then cured using one of the following six methods:

Method 1: A series of four ten (10) second exposures, one on each side of the bracket base, which is a prior art technique.

Method 2: A series of two ten (10) second exposures, one on the mesial side and one on the distal bracket side, which is a modification of the conventional technique in Method 1.

Method 3: A single ten (10) second exposure using the enhancer tip of the present invention.

Method 4: A single twenty (20) second exposure using the enhancer tip of the present invention.

Method 5: A single forty (40) second exposure using the enhancer tip of the present invention.

Method 6: A single twenty (20) second exposure using the second enhancer tip in which there was no internal bevel, e.g., the straight cone device without a beveled surface.

Five replications of each test condition were performed using fresh teeth and brackets for each test. The bond strength values were determined using a universal testing machine (Model TT-B, Instron Engineering Corporation, Canton, Mass.) at a cross head speed of 1.27 millimeters per minute. Debond strength values were determined in units of force from a calibrated strip chart recording. The resulting bonds were subjected to a one-way ANOVA (the independent variable being test method at 6 levels). Fisher's PLSD post-hoc test was performed to compare specific pairs of mean values for significant differences ($p<0.50$).

Figure 3:
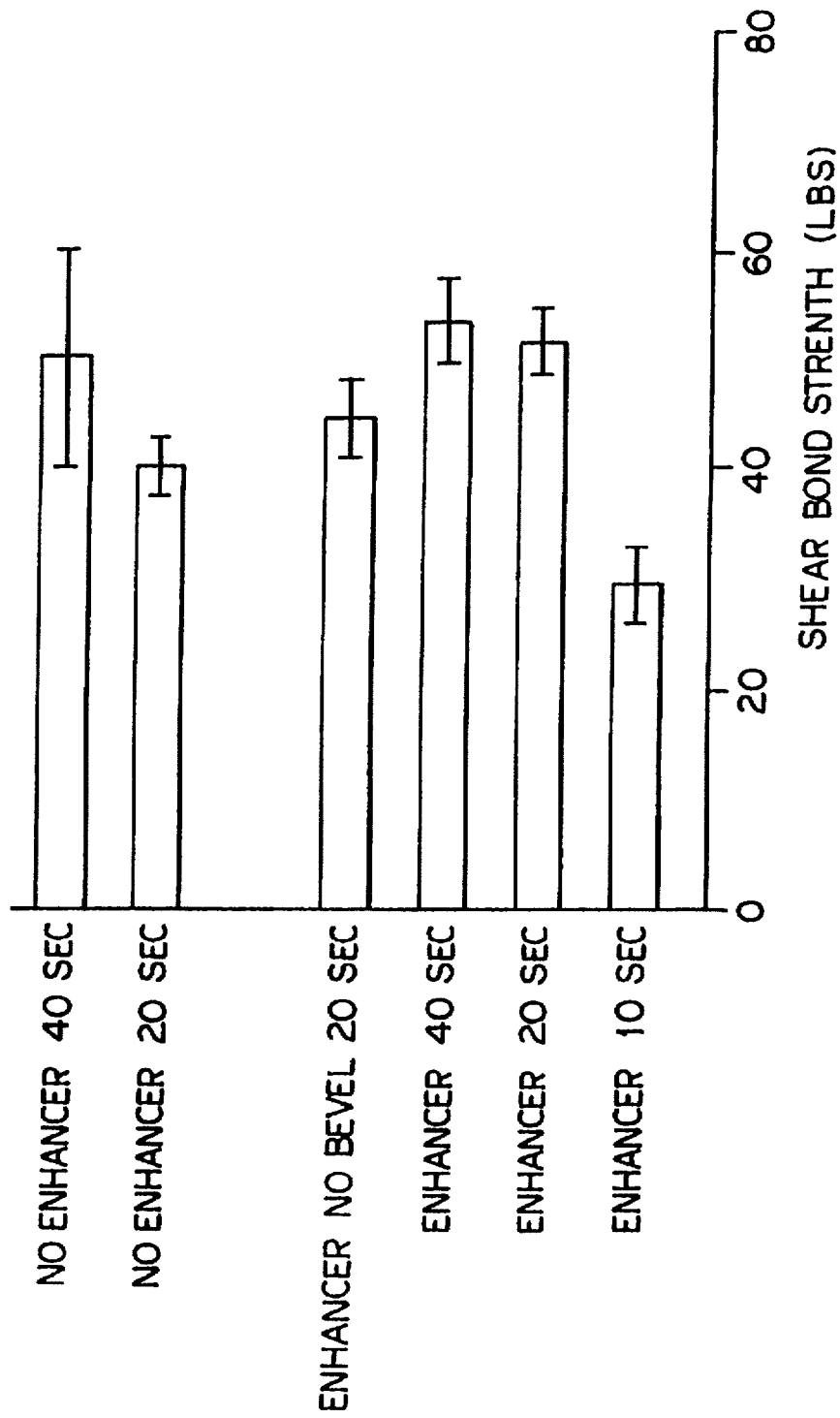
FIG. 3 is a chart of experimental test results performed using a prototype of the present invention compared to a prior art method.

FIG. 3 shows the results of the shear bond strength values for the various test conditions. The first finding was that the conventional method of using four ten-second exposures in Method 1 produced a significantly greater shear bond strength than Method 2, using two ten-second exposures. Thus, it is necessary to provide a forty-second exposure to maximize bond strength using this prior art method. Accordingly, all results obtained with use of the prototype were compared to the exposure condition of Method 1.

A single ten-second exposure using the prototype, tested as Method 3, yielded significantly lower bond strength values compared to the conventional technique of Method 1. Method 3 is, therefore, less desirable than the prior art method in Method 1.

However, a single twenty-second exposure with the prototype of the present invention, as tested in Method 4, yielded statistically similar bond strength results compared to the conventional technique in Method 1. Thus, the clinical time required for bracket bonding using photo-initiation for light curing can be reduced in half using the present invention.

The single forty-second exposure, as tested in Method 5, yielded similar bond strength values compared to using either a single twenty-second exposure with the prototype, as in Method 4, or using the conventional technique of Method 1. Thus, there is no statistical advantage to increase the exposure time when using the enhancer of the present invention to more than twenty seconds.

These tests documented that there was an average increase of eleven (11) pounds in shear bond strength by using a single twenty second exposure with the enhancer of the present invention in Method 4, as compared to using the modified conventional method of giving two ten second exposures without the enhancer as in Method 2. Thus, for a similar exposure time duration of twenty seconds, the prototype of the present invention provided a twenty-eight percent (28%) increase in bond strength.

The data also show that there is an average increase of seven (7) pounds in shear bond strength by using one twenty (20) second exposure with the enhancer of the present invention in Method 4 compared to using one twenty-second (20) exposure with the second enhancer tip in which there was no internal bevel, as in Method 6. Thus, the angled surface provides a significantly greater amount of light at the bracket base to increase resin polymerization.

Of note, these tests were performed using a prototype bore surface that did not have a polished or reflective beveled surface. The surface tested was that aluminum after it had been freshly machined. It is believed that a more highly reflective, beveled surface would provide sufficient clinical bracket strength, and decrease the clinical time required to light-cure brackets—even less than that which was achieved with this prototype.

Although the present invention has been described with reference to specific details of certain embodiments thereof, it is not intended that such details should be regarded as limitations upon the scope of the invention except as and to the extent that they are included in the accompanying claims.

What we claim is:

1. An apparatus for light curing an adhesive resin by use of light on the interface between a bottom surface of an orthodontic bracket and a tooth surface, comprising:
   a. a curing tip enhancer having a body portion with a proximal end and an opposite distal end, the body portion defining a longitudinally-extending bore therethrough, the bore forming an interior surface and being of a size adjacent the distal end to encompass the orthodontic bracket therein; and
   b. means, disposed within the bore of the curing tip enhancer, for directing the light onto the adhesive resin when the orthodontic bracket is disposed within the bore adjacent the distal end.

2. The apparatus of claim 1, wherein the directing means directs the light onto the adhesive in a direction substantially parallel to the bottom surface of the bracket.

3. The apparatus of claim 1, wherein the light emits from a first end of a light source and wherein the apparatus further comprises means for attaching the first end of the light source to the proximal end of the curing tip enhancer so that at least a portion of the light from the light source enters into the bore of the curing tip enhancer.

4. The apparatus of claim 3, wherein the interior surface of the curing tip enhancer adjacent the proximal end has a circumscribing groove therein and the attaching means further comprises an "O" ring disposed in the groove so as to frictionally engage the first end of the light source to the curing tip enhancer.

5. The apparatus of claim 4, wherein the "O" ring is a VITON "O" ring.

6. The apparatus of claim 1, wherein the directing means comprises a portion of the interior surface of the bore adjacent the distal end of the curing tip enhancer being light reflective and being disposed at an acute angle relative to a lower planar surface of the enhancer.

7. The apparatus of claim 6, wherein the interior surface of the bore adjacent the distal end of the curing tip enhancer is disposed at a forty-five degree angle relative to the lower planar surface of the enhancer.

8. The apparatus of claim 6, wherein the interior surface of the bore adjacent the distal end of the curing tip enhancer is a polished metal surface.

9. The apparatus of claim 1, wherein the bore of the curing tip enhancer is circular in cross section.

10. An apparatus for light curing an adhesive resin on an orthodontic bracket disposed on a tooth surface, comprising:
   a. a light source having a first end from which a light emits;
   b. a light enhancer having a body portion with a proximal end on the first end of the light source and an opposite distal end, which defines an opening therein, the body portion defining a longitudinally-extending bore extending therethrough, which communicates within the opening, the bore forming an interior surface, the opening and the bore being of a size adjacent the distal end to receive the orthodontic bracket therein, wherein at least a portion of the light emitting from the light source enters into the bore of the light enhancer adjacent its proximal end; and
   c. means, disposed within the inside surface of the curing tip enhancer, for directing the light within the curing tip enhancer at the adhesive resin when the orthodontic bracket is disposed within the bore through the opening in the distal end.

11. The apparatus of claim 10, wherein the directing means comprises means for focusing the light onto the adhesive in a direction substantially parallel to the bottom surface of the bracket.

12. The apparatus of claim 10, wherein the directing means comprises a portion of the interior surface of the bore adjacent the distal end of the light enhancer being light reflective and being disposed at an acute angle relative to the tooth surface.

13. The apparatus of claim 12, wherein the interior surface of the bore adjacent the distal end of the light enhancer is disposed at a forty-five degree angle relative to the tooth surface.

14. The apparatus of claim 12, wherein the interior surface of the bore adjacent the distal end of the light enhancer is a polished reflective surface.

15. The apparatus of claim 10, wherein the bore of the light enhancer is circular in cross section.

16. A method of light-curing adhesive orthodontic brackets, comprising the steps of:
   a. preparing a tooth surface for disposing an orthodontic bracket having a bottom surface thereon;
   b. placing a desired amount of a visible light-cured bonding adhesive intermediate to the bottom surface of the bracket and the tooth surface;
   c. pressing the bracket onto the prepared tooth surface;
   d. positioning a light source with a light enhancer over the bracket, the light enhancer having a body portion with a proximal end and an opposite distal end, the body portion defining a longitudinally-extending bore therethrough that forms an interior surface, wherein the bore adjacent the distal end is of a size to dispose the bracket therein so that the interior surface of the light enhancer directs the light onto the bracket; and
   e. actuating the light source to cure the adhesive disposed within the bore of the light enhancer for a predetermined time at a selected light intensity.

17. The method of claim 16, wherein the predetermined time is twenty seconds at a selected light intensity of 350 mW/cm$^2$.

* * * * *